United States Patent [19]

Watanabe

[11] 4,343,900

[45] Aug. 10, 1982

[54] PROCESS FOR THE PRODUCTION OF ACRYLAMIDE USING MICROORGANISM

[75] Inventor: Ichiro Watanabe, Yokohama, Japan

[73] Assignee: Nitto Chemical Industry Co., Ltd., Tokyo, Japan

[21] Appl. No.: 194,653

[22] Filed: Oct. 6, 1980

[30] Foreign Application Priority Data

Oct. 4, 1979 [JP] Japan .............................. 54/127389
Oct. 4, 1979 [JP] Japan .............................. 54/127390

[51] Int. Cl.$^3$ .................... C12P 13/02; C12N 11/08; C12R 1/15; C12R 1/365
[52] U.S. Cl. .................................. 435/129; 435/180; 435/872; 435/843
[58] Field of Search ............... 435/129, 174, 177, 180, 435/182, 843, 844, 845, 846, 872

[56] References Cited

U.S. PATENT DOCUMENTS

4,248,968   2/1981   Watanabe et al. .................. 435/129

OTHER PUBLICATIONS

Frobisher, Martin; *Fundamentals of Microbiology,* 7th ed. W. B. Saunders Co., Philadelphia, ©1962, pp. 157–158.

*Primary Examiner*—Raymond N. Jones
*Assistant Examiner*—Elizabeth J. Curtin
*Attorney, Agent, or Firm*—Sughrue, Mion, Zinn, Macpeak & Seas

[57] ABSTRACT

This invention provides a process for the production of acrylamide from acrylonitrile in an aqueous medium by use of a microorganism having nitrilasic activity, wherein at least one compound selected from alkali metal carbonates and bicarbonates is added to the aqueous medium, either solely or in combination with an organic carboxylic acid, thus inhibiting the swelling of fixed cells, maintaining the enzymatic activity for a long period of time, and efficiently obtaining an aqueous solution of acrylamide having high quality.

14 Claims, No Drawings

PROCESS FOR THE PRODUCTION OF ACRYLAMIDE USING MICROORGANISM

BACKGROUND OF THE INVENTION

1. Field of the Invention

This invention relates to an improved process for the production of acrylamide using microorganisms.

2. Description of the Prior Art

It has long been known that microorganisms having nitrilasic activity are effective in hydrolyzing acrylonitrile to yield acrylamide. As such microorganisms, those belonging to the genera Bacillus, Bacteridium in the sense of Prevot, Micrococcus, Brevibacterium in the sense of Bergey, etc., are known (see, for example, U.S. Pat. No. 4,001,081). It has also been discovered by the inventor that those microorganisms belonging to the genera Corynebacterium and Nocardia are also useful for the hydrolysis of acrylonitrile, as described in Japanese Patent Application (OPI) No. 129190/1979 (the term "OPI" as used herein refers to a "published unexamined Japanese patent application").

The production of acrylamide from acrylonitrile by use of such microorganisms is carried out by bringing the microorganism, either as is or after being fixed on a polymeric gel, into contact with acrylonitrile in an aqueous medium (e.g., water, a physiological saline solution, a phosphate buffer solution, etc.). Recently, microorganic reactions using a batchwise or continuous method using granulated fixed cells have been in widespread use for the purposes of the prevention of elution of impurities from the cells, the separation of the cells from a reaction solution, repeated utilization of the cells, an increase in the stability of enzymes, etc. In the production of acrylamide by the use of microorganisms, such methods using granulated fixed cells are advantageous from an economic viewpoint, and the inventors have proposed the production of acrylamide by a continuous column reaction using cells which are fixed by entrapping them with a gel of polyacrylamide, as described in Japanese Patent Application (OPI) No. 143593/1979.

However, the use as an aqueous medium of the above-described physiological saline solution, phosphate buffer solution, etc., is not preferred, in that the acrylamide aqueous solution formed contains large amounts of sodium chloride, phosphoric acid salts, etc., leading to the formation of low quality acrylamide. In particular, when acrylamide of a solution containing phosphoric acid salts is polymerized to produce acrylamide based polymers having high degrees of polymerization, the acrylamide based polymers formed are undesirably liable to become insoluble in water. Therefore, post-treatments such as an ion exchange treatment, etc., become essential for the removal of the phosphoric acid salts prior to polymerization. This leads to the loss of the advantage that a high quality acrylamide aqueous solution can be obtained without providing any special purification step, which is a feature of the method of producing acrylamide by a fixed cells method. Thus, the advantage of the fixed cells method as an inexpensive method for the production of acrylamide is lost.

On the other hand, if the physiological saline solution, phosphate buffer solutions, or the like is not used as the aqueous medium, the fixed cells swell and the enzymatic activity of the cells is rapidly lost. Furthermore, in a continuous hydration reaction of acrylonitrile by use of a column charged with microorganic cells which are fixed by the gel entrapping method, the fixed cells in the column swell in a short time after the start of the reaction, as a result of which efficient operation of the process becomes impossible.

Although the reason why the fixed cells swell during the hydration reaction is not clear, it is believed to be due to the difference in osmotic pressure between the outside and inside of the fixed cells, which results from the difference in concentrations of acrylonitrile and acrylamide between the outside and inside of the cell. This difference is caused to occur when acrylonitrile enters the inside of the fixed cells and is converted or hydrated into acrylamide, and the thus-formed acrylamide goes out of the fixed cells. Furthermore, it is also believed to be due to the facts that the enzyme is liable to leak out of the cell due to swelling and that the stable conformation in normal cells in which the enzyme is not swollen cannot be maintained. Therefore, it is believed that when the reaction is carried out in an isotonic medium comprising a physiological saline solution, a phosphate buffer solution, etc., no great difference in osmotic pressure between the outside and inside of the fixed cells is created, and thus the swelling of the cells of the fixed cells can be prevented.

SUMMARY OF THE INVENTION

As a result of extensive investigations to solve the above-described problems, it has now been found that by carrying out the biological conversion of acrylonitrile into acrylamide in an aqueous medium with a small amount of at least one compound selected from alkali metal carbonates and bicarbonates, and preferably in combination with an organic carboxylic acid, added thereto, an acrylamide aqueous solution having excellent quality can be obtained as a starting material for the production of various polymers, the swelling of fixed cells can be inhibited and the enzymatic activity can be maintained for a long period of time, and furthermore the hydration reaction by the continuous column method using fixed cells can be efficiently carried out for a long period of time.

This invention, therefore, provides a process for producing acrylamide from acrylonitrile in an aqueous medium by the action of microorganisms having nitrilasic activity which process is characterized in that at least one compound selected from the group consisting of alkali metal carbonates and alkali metal bicarbonates is added to the aqueous medium, singly or in combination with an organic carboxylic acid.

DETAILED DESCRIPTION OF THE INVENTION

Any microorganisms capable of hydrolyzing acrylonitrile to yield acrylamide can be used in this invention irrespective of the taxonomical classification thereof. For example, Strain N-771 belonging to the genus Corynebacterium as described in Japanese Patent Application (OPI) No. 129190/1979 (deposited in the Fermentation Research Institute, the Agency of Industrial Science and Technology, Chiba, Japan under the accession number of 4445), Strain N-774 belonging to the genus Corynebacterium (deposited under the accession number of 4446), Strain N-775 belonging to the genus Nocardia (deposited under the accession number of 4447), etc., can preferably be used.

For the fixation of these microorganisms, the entrapping method using gels such as acrylamide based polymers, collagen, gelatin, carrageenan, agar, etc., which is usually in widespread use, can be employed. In this invention, however, the entrapping fixation using acrylamide based polymer gels is particularly preferred from the standpoint of producing acrylamide. By the term "acrylamide based polymers" as used herein is meant those polymers containing as a major component acrylamide, methacrylamide or the like, and, if desired, other ethylenically unsaturated monomers copolymerizable with the major component.

The preparation of fixed cells can be carried out by usual processes. For example, where polyacrylamide gel is used, acrylamide and N,N'-methylenebisacrylamide monomers are mixed with a suspension of cells subjected to a glutaraldehyde treatment, polymerization catalysts of potassium persulfate and dimethylaminopropionitrile are added thereto, and they are reacted under the conditions of a pH of from 6.5 to 8.5, at a temperature of from 0° C. to 10° C., for a period of from 30 to 60 minutes. Thus, a bulky gel containing the cells, i.e., fixed cells entrapped within an acrylamide gel, can be obtained.

Alkali metal carbonates and alkali metal bicarbonates which are added to the aqueous medium according to this invention include sodium carbonate, potassium carbonate, sodium bicarbonate, potassium bicarbonate, etc. The amount of the alkali metal carbonate or bicarbonate being added is 0.01 wt% of more, preferably 0.05 wt% or more, based upon the weight of the aqueous medium containing the acrylonitrile. There are no restrictions on the upper limit of the alkali metal carbonate or bicarbonate that can be added, because even if present in the acrylamide aqueous solution, they exert no substantial adverse influences on the polymerizability of the acrylamide. However, when they are present in large amounts, the problem in the purity of the product arises and moreover, the pH of the acrylamide aqueous solution increases, deteriorating to some extent the enzymatic stability of the fixed cells. Therefore, the amount of the alkali metal carbonate and bicarbonate added is adjusted to about 0.5% or less, based on the weight of the aqueous medium and the pH of the aqueous medium is adjusted to from about 6.5 to 9.5, and preferably to from 7.5 to 8.5.

When the organic carboxylic acid is added in combination with the alkali metal carbonate or bicarbonate, the amount of the alkali metal carbonate or bicarbonate to be added should be sufficient to neutralize the organic carboxylic acid and to keep the pH within the above range. For example, when the sodium carbonate and the acrylic acid are used, the weight ratio ranges of the sodium carbonate to the acrylic acid is from about 1.3:1 to about 1.7:1.

As such organic carboxylic acids, any of monocarboxylic acids, dicarboxylic acids, tricarboxylic acids, unsaturated carboxylic acids, oxycarboxylic acids, etc., can be used so long as they are water-soluble. Examples include formic acid, acetic acid, propionic acid, butyric acid, valerianic acid, oxalic acid, malonic acid, succinic acid, glutaric acid, adipic acid, acrylic acid, methacrylic acid, crotonic acid, fumaric acid, maleic acid, itaconic acid, glucoric acid, hydroxypropionic acid, lactic acid, malic acid, tartaric acid, citric acid, gluconic acid, etc. Practically preferred examples include formic acid, acetic acid, propionic acid, acrylic acid, etc. The amount of the organic carboxylic acid added is 0.005% or more, preferably 0.01% or more, based upon the weight of the aqueous medium containing the acrylonitrile. When they are present in such small amounts, they exert no substantial adverse influences onto the polymerizability of acrylamide. However, when they are present in large amounts, the purity of the product may be reduced and, therefore, they are preferably added in an amount of 1% or less, based upon the acrylamide.

In the practice of this invention, the above prepared polyacrylamide gel-entrapped cells are pulverized to particles of a suitable size and, after being washed, are charged to a column reactor. By passing a substrate solution prepared by mixing the aqueous medium containing at least one compound selected from the alkali metal carbonates and bicarbonates, singly or in combination with the organic carboxylic acid, and acrylonitrile through the column, the aqueous acrylamide solution medium can be obtained as a column effluent.

Additionally, the reaction can be controlled by selecting the amount of the cells, the concentration of substrate acrylonitrile, the flow rate, etc., to obtain a conversion of nearly 100%. In this case, to maintain the nitrilasic activity of the fixed cells for a long period of time and to inhibit the formation of by-products such as acrylic acid, etc., it is preferred that the concentration of acrylonitrile be 5% by weight or less, that the reaction temperature be as low as possible within a range such that the substrate aqueous solution does not freeze, i.e., from just above the freezing point to 10° C., and that the pH be from 7.5 to 8.5.

Thus, a colorless, transparent acrylamide aqueous solution can be obtained as a reaction effluent. Since this acrylamide aqueous solution contains almost no impurities that exert adverse influences on the polymerization of acrylamide, it can be used, as is or after being concentrated, as a starting material for the production of acrylamide polymers for use in flocculants, paper strengthening agent, etc.

The following examples and comparative examples are given to illustrate this invention in greater detail. All parts and percents are by weight. The acrylonitrile, acrylamide, acrylic acid concentrations were measured by gas chromatography.

EXAMPLE 1 AND COMPARATIVE EXAMPLE 1

To 40 parts of the resting cells (water content 75%) of Strain N-774 aerobically cultured on a culture medium (pH 7.2) containing 1% of glucose, 0.5% of peptone, 0.3% of yeast extract and 0.3% of malt extract were added 0.4 part of a 50% aqueous solution of glutaraldehyde and 9.6 parts of a 0.05 M phosphate buffer solution (pH 8.0), and the reaction was carried out with stirring at 10° C. or less for 1 hour. To this reaction solution were added 9.5 parts of acrylamide, 0.5 part of N,N'-methylenebisacrylamide and 25 parts of water to give a uniform suspension. A mixture of 5 parts of a 5% aqueous solution of dimethylaminopropionitrile and 10 parts of a 2.5% aqueous solution of potassium persulfate was added to the above-prepared suspension, and they were polymerized by maintaining the mixture at 10° C. or less for 1 hour. The thus-obtained bulky cell-containing gel was pulverized and fully washed with a 0.1% aqueous solution of acrylic acid, which had been neutralized with sodium carbonate to pH 8.0, to thereby obtain 100 parts of the fixed cells.

Three jacketed glass columns, each column being charged with 40 parts of the above-prepared fixed cells, were connected in series. A mixed solution of 4 parts of acrylonitrile and 96 parts of a 0.1% aqueous solution of sodium acrylate (neutralized with $Na_2CO_3$ to pH 8.0)

was introduced into the first column (hereinafter referred to as "Column No. 1") from the top thereof, and passed therethrough at a temperature of 5° C. and SV (Space Velocity)=0.8 hr$^{-1}$. 96 parts of the reaction solution flowing out of Column No. 1 was mixed with 4 parts of acrylonitrile, introduced into the second column (hereinafter referred to as "Column No. 2") from the top thereof, and passed therethrough at SV=0.8 hr$^{-1}$. The effluent from the bottom of Column No. 2 in the amount of 96.5 parts was mixed with 3.5 parts of acrylonitrile, introduced into the third column (hereinafter referred to as "Column No. 3") from the top thereof, and passed therethrough at a temperature of 5° C. and SV=0.8 hr$^{-1}$. The reaction in each column proceeds smoothly without causing the trouble resulting from the swelling of the fixed cells. As an effluent from the bottom of Column No. 3, a 15.4% aqueous solution of acrylamide containing no acrylonitrile was obtained. This aqueous solution was vacuum-concentrated at 45° C. by use of a flash evaporator while bubbling air therethrough, to thereby obtain a concentrated solution having an acrylamide concentration of 28%.

A mixture of 657 parts of the above-obtained acrylamide aqueous solution (concentration 28%) and 135 parts of deionized water was placed in a polymerization reactor, and 4.8 parts of boric acid and 3.2 parts of sodium hydroxide (NaOH) were added thereto. Furthermore, 0.032 part of dimethylaminopropionitrile and 0.032 part of potassium persulfate were added, and the polymerization was carried out at 25° C. in a nitrogen atmosphere. After an induction period of about 15 minutes, the polymerization proceeded smoothly and a polymerization product was obtained in a gel form. This polymerization product was cut into small particles and dried at 90° C. for 16 hours and further at 60° C. for 16 hours, to thereby obtain a granular polymer. This granular polymer had a 0.1% aqueous solution viscosity of 700 cps and a degree of hydrolysis of 12.5%; thus it had excellent characteristics as a flocculant.

For comparison, the procedure of Example 1 was repeated with the exception that as an aqueous solution for use in washing the fixed cells gel and in dissolving acrylonitrile, a 0.05 M phosphate buffer solution (pH 8) was used. The thus-obtained 28% aqueous solution of acrylamide was polymerized in the same manner as in Example 1, and the polymerization proceeded smoothly in nearly the same manner as in Example 1. However, when a 0.1% aqueous solution of the granular polymer obtained by drying was prepared, large amounts of insoluble gels remained. While the viscosity and the degree of hydrolysis were 550 cps and 13.0%, respectively, when it was used as a flocculant, its aggregation properties were inferior.

EXAMPLE 2 AND COMPARATIVE EXAMPLE 2

Fixed cells (Strain N-774) prepared in the same manner as in Example 1 were charged into the same column reactor as in Example 1, and a substrate solution consisting of 3 parts of acrylonitrile and 97 parts of a 0.1% aqueous solution of sodium acrylate (neutralized with Na$_2$CO$_3$ to pH 8.0) was introduced into the column reactor from the top of Column No. 1 at a temperature of 5° C. and SV=0.8 hr$^{-1}$. In the same manner as in Example 1, 97 parts of an effluent from the bottom of Column No. 1 was mixed with 3 parts of acrylonitrile and the resulting mixture was then introduced into Column No. 2 from the top thereof, and the same procedure was repeated in the case of Column No. 3. Thus, a reaction solution containing 12.0% of acrylamide and 0.03% of acrylic acid (pH 8.0) was obtained from the bottom of Column No. 3. The reaction was continued continuously for 10 days, during which time no unreacted acrylonitrile was detected in the effluent from Column No. 3.

For comparison, the procedure of Example 2 was repeated with the exception that as an aqueous solution for use in dissolving acrylonitrile, a 0.85% physiological saline solution neutralized with NaOH to pH 8.0 was used. The reaction solution obtained from the bottom of Column No. 3 contained 11.5% of acrylamide and 0.5% of acrylic acid, and had a pH of 6.9. Thus, it can be seen that acrylic acid was by-produced in a large amount. After the reaction was continued continuously for 10 days, the effluent from the bottom of Column No. 3 was examined and it was found that a large amount of acrylonitrile (about 3% in the reaction solution) was contained. Although a smooth operation with no swelling of the fixed cells was attained, the reduction in the activity was found to be significant.

EXAMPLES 3 TO 7 AND COMPARATIVE EXAMPLES 3 TO 5

A fixed cells (Strain N-774) prepared in the same manner as in Example 1 was charged into the same column reactor as in Example 1, and a substrate solution prepared by mixing 3 parts of acrylonitrile and 97 parts of an aqueous solution containing the salt obtained by neutralizing the organic carboxylic acid as indicated in Table 1 with Na$_2$CO$_3$ or NaHCO$_3$ was introduced into the column reactor from the top of Column No. 1 at a temperature of 5° C. and SV=0.5 hr$^{-1}$. The same procedure as in Example 1 was repeated to thereby obtain an acrylamide aqueous solution. The acrylamide aqueous solution thus-obtained was concentrated, and the concentrated solution was then polymerized. The physical properties and aggregation properties of the polymer obtained were evaluated. After the reaction was continued continuously for 10 days, the concentration of acrylonitrile in the reaction solution was measured.

For comparison, the same procedure as above was repeated with the exception that as an aqueous medium for use in dissolving acrylonitrile, a solution prepared by neutralizing pure water with NaOH to pH 8.0 (Comparative Example 3), a solution prepared by neutralizing a 0.85% physiological saline solution with NaOH to pH 8.0 (Comparative Example 4), or a 0.05 M phosphate buffer solution (Comparative Example 5) was used.

The results are shown in Table 1. It can be seen from the results of Table 1 that the method of this invention is effective in maintaining the enzymatic activity for a long period of time and permits the production of acrylamide having excellent quality.

TABLE 1

| | Example 3 | Example 4 | Example 5 | Example 6 | Example 7 | Comparative Example 3 | Comparative Example 4 | Comparative Example 5 |
|---|---|---|---|---|---|---|---|---|
| Composition of aqueous solution | 0.1% acrylic acid | 0.1% acrylic acid | 0.1% acetic acid | 0.1% propionic | 0.1% malic acid | pure water | 0.85% physiologi- | 0.05M phosphate |

TABLE 1-continued

|  | Example 3 | Example 4 | Example 5 | Example 6 | Example 7 | Comparative Example 3 | Comparative Example 4 | Comparative Example 5 |
|---|---|---|---|---|---|---|---|---|
| used in dissolving substrate | neutralized with $Na_2CO_3$ to pH 8.0 | neutralized with $Na_2CO_3$ plus $NaHCO_3$ to pH 8.0 | neutralized with $Na_2CO_3$ to pH 8.0 | acid neutralized with $Na_2CO_3$ to pH 8.0 | neutralized with $Na_2CO_3$ to pH 8.0 |  | cal saline solution | buffer solution |
| pH of 3% substrate solution | 8.0 | 8.0 | 8.0 | 8.0 | 8.0 | 8.0 (adjusted with NaOH) | 8.0 (adjusted with NaOH) | 8.0 |
| Swelling of fixed cells during reaction | not occurred | not occurred | not occurred | not occurred | not occurred | occurred | not occurred | not occurred |
| Acrylonitrile in effluent after continuous operation for 10 days | none | none | none | none | none | about 8% in the reaction solution | about 3% in the reaction solution | none |
| Formed acrylamide |  |  |  |  |  |  |  |  |
| Polymerizability | A | A | A | A | A | A | A | B |
| Solubility | A | A | A | A | A | A | B | x |
| Aggregation properties | A | A | A | A | A | A | B | x |

A: good, B: fair, x: poor

EXAMPLE 8 AND COMPARATIVE EXAMPLE 6

The procedure of Example 1 was repeated with the exception that a 0.1% aqueous solution of $NaHCO_3$ was used in place of the 0.1% aqueous solution of sodium acrylate (neutralized with $Na_2CO_3$ to pH 8.0). The reaction in each column proceeded smoothly without causing the swelling of the fixed cells. From the bottom of Column No. 3, a 15.4% aqueous solution of acrylamide substantially not containing unreacted acrylonitrile and by-produced acrylic acid was obtained as an effluent. This aqueous solution was vacuum-concentrated while bubbling air therethrough at 45° C. by use of a flash evaporator to thereby obtain a 30.0% aqueous solution of acrylamide. The thus-obtained acrylamide aqueous solution could be used as is as a starting material for the production of various acrylamide based polymers.

For comparison, the reaction and condensation were carried out in the same manner as above (Example 8) with the exception that a 0.05 M phosphoric acid buffer solution (pH 8.2) was used as an aqueous solution for use in dissolving acrylonitrile, to thereby obtain a 30.0% aqueous solution of acrylamide. This acrylamide aqueous solution was used as is to produce polyacrylamide. The thus-obtained polyacrylamide was exceptionally poor in its solubility in water and inferior as a flocculant.

EXAMPLE 9 AND COMPARATIVE EXAMPLE 7

The fixed cells (Strain N-774) prepared in the same manner as in Example 1 was charged to the same column reactor as in Example 1, and a substrate solution consisting of 3 parts of acrylonitrile and 97 parts of a 0.2% $NaHCO_3$ aqueous solution was introduced into the column reactor from the top of Column No. 1 at a temperature of 5° C. and SV=0.5 hr$^{-1}$. In the same manner as in Example 1, 97 parts of an effluent from the bottom of Column No. 1 was mixed with 3 parts of acrylonitrile and the resulting mixture was then introduced into Column No. 2 from the top thereof, and the same procedure was repeated in the case of Column No. 3. Thus, a reaction solution (pH 8.2) containing 12.0% of acrylamide and 0.02% of acrylic acid was obtained from the bottom of Column No. 3. The reaction was continued for 10 days, but no acrylonitrile was detected in the effluent from Column No. 3.

For comparison, a reaction was carried out in the same manner as in foregoing Example 9 with the exception that as an aqueous solution for use in dissolving acrylonitrile, a solution prepared by neutralizing a physiological saline solution (NaCl concentration: 0.85%) with NaOH to pH 8.2 was used. The reaction solution obtained from the bottom of Column No. 3 contained 11.5% of acrylamide and 0.5% of acrylic acid, and had a pH of 6.9. Thus, it can be seen that acrylic acid was by-produced in a large amount. After the reaction was continued for 10 days, the effluent from the bottom of Column No. 3 was examined and it was found that a large amount of unreacted acrylonitrile was contained and the activity of the fixed cells was markedly reduced.

EXAMPLE 10

The fixed cells (Strain N-774) prepared in the same manner as in Example 1 was charged to the same column reactor as used in Example 1, and a substrate solution consisting of 3 parts of acrylonitrile and 96 parts of an aqueous solution (pH 8.4) containing 0.2% of $NaHCO_3$ and 0.005% of $Na_2CO_3$ was introduced into the column reactor from the top of Column No. 1 at a temperature of 0° C. and SV=0.5 hr$^{-1}$. The same procedure as in Example 1 was repeated, to thereby obtain a 12.1% acrylamide aqueous solution from the bottom of Column No. 3.

The aqueous solution contained no acrylonitrile, and acrylic acid was almost undetected. After the reaction was continued for 10 days, the reaction solution was examined, and it was found that the concentration of acrylamide was 12.1% and that acrylonitrile and acrylic acid were not detected at all. The thus-obtained effluent was vacuum-concentrated while bubbling air at a temperature of 45° C. by use of a flash evaporator to thereby obtain a 30.0% aqueous solution of acrylamide. This acrylamide aqueous solution could be used as is as a starting material for the production of various acrylamide based polymers.

While the invention has been described in detail and with reference to specific embodiments thereof, it will be apparent to one skilled in the art that various changes and modifications can be made therein without departing from the spirit and scope thereof.

What is claimed is:

1. A process for preparing acrylamide from acrylonitrile in an aqueous medium containing a microorganism having nitrilasic activity, which comprises adding from 0.01% to 0.5% by weight, based on the weight of the aqueous medium containing the acrylonitrile, of at least one compound selected from the group consisting of alkali metal carbonates and bicarbonates to the aqueous medium, wherein pH is from 6.5 to 9.5 and said process is conducted for a period of time sufficient to convert said acrylonitrile to said acrylamide.

2. A process as in claim 1 wherein the compound is added in combination with an organic carboxylic acid.

3. A process as in claim 1 or 2 wherein the alkali metal carbonates and bicarbonates are selected from the group consisting of sodium bicarbonate, potassium bicarbonate, sodium carbonate and potassium carbonate.

4. A process as in claim 2 wherein the organic carboxylic acid is selected from the group consisting of formic acid, acetic acid, propionic acid, butyric acid, valerianic acid, oxalic acid, malonic acid, succinic acid, glutaric acid, adipic acid, acrylic acid, methacrylic acid, crotonic acid, fumaric acid, maleic acid, itaconic acid, gluconic acid, hydroxypropionic acid, lactic acid, malic acid, tartaric acid, citric acid, and gluconic acid.

5. A process as in claim 2 wherein the organic carboxylic acid is selected from the group consisting of formic acid, acetic acid, propionic acid, and acrylic acid.

6. A process as in claim 1 or 2 wherein the microorganism having nitrilasic activity is selected from microorganisms belonging to the genera Corynebacterium and Nocardia.

7. A process as in claim 6 wherein the microorganism is selected from Strains N-771 belonging to the genus Corynebacterium, N-774, and N-775 belonging to the genus Nocardia.

8. A process as in claim 1 or 2 wherein the microorganism is fixed on a polyacrylamide based gel.

9. A process as in claim 1 or 2 wherein the temperature of the aqueous medium is from above the freezing point of the medium to 10° C.

10. A process as in claim 1 or 2 wherein the pH of the aqueous medium is from 7.5 to 8.5.

11. A process as in claim 2 wherein the amount of the organic carboxylic acid added is from 0.005% to 1% by weight.

12. A process as in claim 1 or 2 wherein at least 0.05% by weight of the compounds selected from the group consisting of alkali metal carbonates and bicarbonates is added to the aqueous medium.

13. A process as in claim 1 wherein the concentration of acrylonitrile is 5% by weight or less.

14. A process as in claim 13 wherein the temperature is from just above the freezing point of the aqueous medium to 10° C.

* * * * *